(12) United States Patent
Simmons et al.

(10) Patent No.: US 10,927,397 B2
(45) Date of Patent: Feb. 23, 2021

(54) COMPOSITIONS, DEVICES AND METHODS FOR DETECTING BIOFILMS (71) Applicant: Sterilex, LLC, Hunt Valley, MD (US)

(72) Inventors: Ryan Alexander Simmons, Baltimore, MD (US); Edward Fu, Cranberry Township, PA (US)

(73) Assignee: Sterilex, LLC, Hunt Valley, MD (US)

( * ) Notice: Subject to any disclaimer, the term of this patent is extended or adjusted under 35 U.S.C. 154(b) by 0 days.

(21) Appl. No.: 16/654,745

(22) Filed: Oct. 16, 2019

(65) Prior Publication Data

US 2020/0115733 A1 Apr. 16, 2020

Related U.S. Application Data (60) Provisional application No. 62/746,262, filed on Oct. 16, 2018.

(51) Int. Cl.
*C12Q 1/04* (2006.01)
*G01N 21/77* (2006.01)

(52) U.S. Cl.
CPC ............ *C12Q 1/04* (2013.01); *G01N 21/77* (2013.01)

(58) Field of Classification Search
CPC ............................................... C12Q 1/04
See application file for complete search history.

(56) References Cited

U.S. PATENT DOCUMENTS

| | | | |
|---|---|---|---|
| 3,449,431 A | 6/1969 | Swenson | |
| 5,208,257 A | 5/1993 | Kabara | |
| 5,486,315 A * | 1/1996 | Tseng | C07C 291/04 510/480 |
| 6,022,551 A | 2/2000 | Jampani et al. | |
| 6,025,312 A | 2/2000 | Saito et al. | |
| 6,096,225 A | 8/2000 | Yang et al. | |
| 6,107,261 A | 8/2000 | Taylor et al. | |
| 6,110,883 A | 8/2000 | Petri et al. | |
| 6,555,055 B1 | 4/2003 | Cisar et al. | |
| 6,630,172 B2 | 10/2003 | Batarseh | |
| 6,673,761 B2 | 1/2004 | Mitra et al. | |
| 6,800,478 B2 | 10/2004 | Castellini | |
| 6,827,795 B1 | 12/2004 | Kasturi et al. | |
| 6,939,566 B2 | 9/2005 | Batarseh et al. | |
| 7,674,602 B2 | 3/2010 | Kadurugamuwa et al. | |
| 8,425,945 B2 | 4/2013 | Barraud et al. | |
| 8,784,659 B2 | 7/2014 | Whitekettle et al. | |
| 8,888,926 B2 | 11/2014 | Dooley et al. | |
| 9,012,167 B2 | 4/2015 | Dallenne et al. | |
| 9,023,374 B2 | 5/2015 | Touitou | |
| 9,393,249 B2 | 7/2016 | Barrett et al. | |
| 9,441,204 B2 | 9/2016 | Voorhees et al. | |
| 9,518,246 B2 | 12/2016 | Tachikawa et al. | |
| 9,535,043 B2 | 1/2017 | Manion et al. | |
| 9,540,594 B2 | 1/2017 | Gonzales et al. | |
| 9,593,160 B2 | 3/2017 | Ingber et al. | |
| 9,637,770 B2 | 5/2017 | Kotzer et al. | |
| 9,707,162 B2 | 7/2017 | De Szalay | |
| 9,707,520 B2 | 7/2017 | Denvir et al. | |
| 9,771,547 B2 | 9/2017 | Hulskotter et al. | |
| 9,826,770 B2 | 11/2017 | Scholz et al. | |
| 9,961,886 B2 | 5/2018 | Ala'Aldeen et al. | |
| 10,138,117 B2 * | 11/2018 | Chen | H01L 21/02063 |
| 2004/0053803 A1 | 3/2004 | Lye et al. | |
| 2004/0067861 A1 | 4/2004 | DeNome et al. | |
| 2005/0058602 A1 | 3/2005 | Ramji et al. | |
| 2005/0084471 A1 | 4/2005 | Andrews et al. | |
| 2005/0246849 A1 | 11/2005 | Minkler et al. | |
| 2006/0122089 A1 | 6/2006 | Lambotte et al. | |
| 2006/0171907 A1 | 8/2006 | Scott et al. | |
| 2006/0257281 A1 | 11/2006 | Weide et al. | |
| 2006/0264355 A1 | 11/2006 | Storr et al. | |
| 2007/0292370 A1 | 12/2007 | Clarot et al. | |
| 2007/0292371 A1 | 12/2007 | Clarot et al. | |
| 2007/0298991 A1 | 12/2007 | Longo | |
| 2008/0193650 A1 | 8/2008 | Lyon | |
| 2008/0255498 A1 | 10/2008 | Houle | |
| 2010/0144579 A1 | 6/2010 | Völkel et al. | |
| 2011/0081628 A1 | 4/2011 | Alden, IV et al. | |
| 2012/0301522 A1 | 11/2012 | Prosise et al. | |
| 2013/0029884 A1 | 1/2013 | Malchesky et al. | |
| 2014/0248373 A1 | 9/2014 | Michalow et al. | |

(Continued)

FOREIGN PATENT DOCUMENTS

| | | | |
|---|---|---|---|
| EP | 2902497 A1 | 8/2015 | |
| EP | 3214180 A1 | 9/2017 | |

(Continued)

OTHER PUBLICATIONS

Beltrán-García, Miguel Juan, et al. "Catalasas de hongos fitopatogenos:¿ factores de virulencia y resistencia a los fungicidal?." *Revista Mexicana de Fitopatología* 24.1 (2006): 50-58.
https://www.betelgeux.es > news > tbf-300-patent, accessed Jun. 20, 2017.
Cochran, Wendy L., Gordon A. McFeters, and P. S. Stewart. "Reduced susceptibility of thin Pseudomonas aeruginosa biofilms to hydrogen peroxide and monochloramine." *Journal of applied microbiology* 88.1 (2000): 22-30.

(Continued)

*Primary Examiner* — Bin Shen (74) *Attorney, Agent, or Firm* — Frost Brown Todd LLC (57) ABSTRACT Generation of foam when spraying biofilm-detection compositions onto a surface may entrain air and create bubbles, which lead to false positives. Aqueous biofilm-detecting compositions containing low-foaming surfactants, radical scavenger, solvent, thickener, hydrogen peroxide, chelating and coupling agent may be sprayed onto a surface to test for the presence of biofilm without generating excess bubbles or foam.

12 Claims, 1 Drawing Sheet (56) References Cited

U.S. PATENT DOCUMENTS

| | | |
|---|---|---|
| 2014/0369953 A1 | 12/2014 | Purschwitz et al. |
| 2015/0132796 A1 | 5/2015 | Boels et al. |
| 2015/0210964 A1 | 7/2015 | Willey et al. |
| 2016/0152928 A1 | 6/2016 | Weber et al. |
| 2016/0235636 A1 | 8/2016 | Fischer et al. |
| 2016/0265023 A1 | 9/2016 | Manion et al. |
| 2016/0304886 A1 | 10/2016 | Rickard et al. |
| 2016/0311877 A1 | 10/2016 | Watters et al. |
| 2017/0181429 A1 | 6/2017 | Luciow et al. |
| 2017/0281694 A1 | 10/2017 | Gantz et al. |
| 2018/0027812 A1 | 2/2018 | Bobbert et al. |
| 2018/0105861 A1 | 4/2018 | Desrosiers et al. |
| 2018/0242578 A1 | 8/2018 | Li et al. |

FOREIGN PATENT DOCUMENTS

| | | | |
|---|---|---|---|
| FR | 2611744 A1 | 9/1988 | |
| JP | S61162199 A | 7/1986 | |
| JP | 2005-210997 A | 8/2005 | |
| WO | WO 2004/003124 A1 | 1/2004 | |
| WO | WO 2013/030419 A1 | 3/2013 | |
| WO | WO-2014049182 A1 * | 4/2014 | ............... C12Q 1/30 |
| WO | WO 2017/072482 A1 | 5/2017 | |
| WO | WO 2017/177142 A1 | 10/2017 | |
| WO | WO 2017/177342 A1 | 10/2017 | |
| WO | WO 2018/002100 A1 | 1/2018 | |

OTHER PUBLICATIONS

Galie, Serena, et al. "Biofilms in the food industry: health aspects and control methods." *Frontiers in microbiology* 9 (2018): 898.

Atsushi Kawabe, Control of Biofilm for the Seawater Pipes, *Bulletin of the Society of Sea Water Science*, Japan, 2012, vol. 66, Issue 4, pp. 209-220.

* cited by examiner

COMPOSITIONS, DEVICES AND METHODS FOR DETECTING BIOFILMS

PRIORITY

This application claims priority to U.S. Provisional Patent Application No. 62/746,262, entitled "Compositions, Devices and Methods for Detecting Biofilms," filed Oct. 16, 2018, the disclosure of which is incorporated by reference herein.

BACKGROUND

A biofilm is an assemblage of microbes that is associated with a surface and is usually enclosed in an extracellular matrix of polysaccharide material of microbial origin. A biofilm may be composed of microbial cells of a single species or multiple species. Bacteria commonly found in biofilms include, but are not limited to, *Pseudomonas, Listeria, Escherichia, Salmonella, Enterobacter, Flavobacterium, Alcaligenes, Staphylococcus* and *Bacillus*. Fungi, including but not limited to yeast, may also form biofilms, an occurrence that is common in the wine industry.

Extracellular polymeric matrices of polysaccharide material play various roles in the structure and function of biofilm communities. For example, extracellular matrices may provide for a stable environment that promotes cellular growth and proliferation, adhesion of cells to surfaces and/or to each other, protection against antimicrobial agents, promotion of the acquisition of new genetic traits, and/or improved nutrient availability and metabolic co-operability. In sum, the extracellular polymeric matrices may make it difficult to disrupt and/or to remove biofilm from a surface, particularly the surfaces in hard-to-reach areas such as in niches and crevasses.

Biofilms are responsible for a wide variety of microbial infections of the body. Thus, the presence of biofilms in environments in which hygiene is important is highly undesirable. Such environments include but are not limited to hospitals (including on medical devices), in the food and beverage industry (e.g., in food and/or beverage processing plants, delis, restaurants, dairies), in industrial refrigeration systems and drinking water pipes; and domestic environments (e.g., in bathrooms and kitchens).

For the foregoing reasons, it is essential and often mandated by governmental regulation, to implement hygiene systems that disrupt and/or remove biofilms from surfaces. A key factor in implementing hygiene systems is the ability to monitor for their presence. Rapid monitoring methods include commercially available products that rely upon a reaction of hydrogen peroxide with biofilms by means of enzymes present in the microorganisms.

For example, EP 2902497A1, which is entitled "Use of Hydrogen Peroxide Compositions for Detecting Biofilms" (hereinafter, "Itram"), describes a hydrogen peroxide-containing solution that reacts with catalase to generate water and oxygen gas. According to Itram, effervescence due to the release of oxygen gas acts as an indicator of the presence of microorganisms. To aid in visualizing the presence of oxygen gas on a tested surface, Itram includes high-foaming surfactant(s) in its disclosed biofilm detection compositions. Itram indicates that the foaming effect of the foaming surfactant facilitates the viewing of the effervescence, due to the retention of the bubbles produced by the oxygen released during the reaction between hydrogen peroxide and the catalase generated from the microorganisms that form the biofilm.

U.S. Pat. Pub. No. 2018/0105861 A1, which is entitled "Methods, Compositions and Kits for Determining Cleanness of a Surface" (hereinafter, "Desrosiers")," describes a developer solution comprising hydrogen peroxide that is used to detect the presence of enzyme, particularly catalase, that has been previously deposited onto a surface via treatment of the surface with an "enzyme solution." Desrosiers' developer solution contains one or more foaming agents that are said to improve the visual effect of the developer solution for detection of enzyme on the treated surface.

Solutions including, but not limited to, the biofilm detection solutions described above, are sprayed onto a surface to be tested for the presence of biofilm or enzyme. As a result of being dispensed through a nozzle, the biofilm-detecting solutions may be subject to high shear conditions, which may promote entrainment of air in the solution, causing air bubbles to occur. The inclusion of foaming agents, i.e., high-foaming surfactants, in the prior art biofilm-detecting solutions, may cause air bubble formation upon spraying and may contribute to stability of the bubbles formed during spraying. As a result, air bubbles may be deposited onto the surface to be tested, thus resulting in a false positive for a biofilm.

Compositions for treating or eliminating biofilms, microbes and/or germs are also known.

For example, U.S. Pat. Pub. No. 2015/0210964 A1, which is entitled "Consumer Product Compositions" (hereinafter, "Willey"), describes a consumer product compositions that are said to be effective to eliminate biofilm. The consumer product compositions are photocatalyzable and comprise water soluble organic photoactivator, an electron acceptor which accepts an electron from the photoactivator when the photoactivator is in a photo-excited state and/or reduced state, and a benefit active precursor, e.g., oxyhalite, which converts into a benefit active agent, e.g., chlorine dioxide, via electron transfer. Willey's compositions are preferably substantially colorless. Willey discloses a method of removing biofilm comprising the steps of contacting the biofilm with a consumer product composition of the disclosed invention and exposing the consumer product composition to light, preferably having a wavelength greater than about 350 nm.

U.S. Pat. Pub. No. 2018/0242578 A1, which is entitled "Generation of Peroxyformic Acid Through Polyhydric Alcohol Formate" (hereinafter, "Li"), describes compositions for the in-situ generation of peroxyformic acid for several uses, including treating biofilm. According to Li, the peroxyformic acid is generated in-situ from two reagents, an ester of a polyhydric alcohol and formic acid and a hydrogen peroxide source. The two reagents are kept apart until just prior to use, given the inherent instability of peroxyformic acid in storage and its explosive nature. Thus, on-site generation of peroxyformic acid is undertaken to treat biofilm.

U.S. Pat. No. 9,707,162 B2, which is entitled "Microbicidal Personal Care Compositions Comprising Metal Ions" (hereinafter, "De Szalay"), is directed to animate surface treatment compositions comprising a metal ion source that releases copper ions and/or zinc ions into the treatment composition. Certain embodiments, optionally but very preferably, also include at least one detersive surfactant.

U.S. Pat. Pub. No. 2005/0246849 A1, which is entitled "Sanitizing Handle for Cleaning Tool" (hereinafter, "Minkler"), describes a cleaning implement with a handle that has an antimicrobial surface. Minkler indicates that in one embodiment, the cleaning device comprises a cleaning pad that is impregnated with a cleaning composition that is "wet-to-the-touch." In another embodiment, Minkler indicates that the cleaning device comprises a cleaning pad that is impregnated with a cleaning composition that is "dry-to-the-touch," i.e., it is that the substrate is free of water or other solvents in an amount that would make them feel damp or wet-to-the-touch as compared to the touch of a wet substrate. Minkler's cleaning implement can include "biosensors" that are biocatalytic or bioaffinity sensors that provide a signal, e.g., visual or electrical, for the presence of the presence of an enzyme, organelle, tissue, etc. to the user of the cleaning implement.

U.S. Pat. Pub. No. 2008/0255498 A1, which is entitled "Sensitizer Solutions, Systems, and Methods of Use" (hereinafter, "Houle"), is directed to a kit cleaning system and method that may be used to clean an oral or skin surface site on which a biofilm may be present. It is said that a delivery system is configured to dispense a treatment solution at a treatment site, the dispensed treatment solution comprising a carrier including a sensitizer, a chemical species, and a solvent within which the chemical species is soluble; and an activation device configured to deliver energy to the treatment solution at the treatment site, where the delivered energy is within a range appropriate to cause the sensitizer to promote the formation of a reactive chemical species from the chemical species. In certain embodiments a transducer, such as an acoustic transducer, produces temperature elevation, the formation and/or collapse of microbubbles, and/or rapid expansion (e.g., expansion of a gas contained in microbubbles, boiling: conversion of liquid forms into gaseous forms), and/or cavitation in the sensitizer solution 12 and/or surrounding tissue structures and/or fluids.

A need remains for biofilm-detecting solutions that have low-foaming properties such that when they are subject to spraying, they reduce or eliminate false positives for biofilms. It would further be desirable for biofilm-detecting solutions to have sufficient viscosity to cling to surfaces, including vertical surfaces, while being sprayed over large surface areas. It would further be desirable for biofilm-detecting solutions to be characterized by viscosity that is stable over time. It would further be desirable for biofilm-detecting solutions to be ready-to-use, thus requiring no premixing in situ and/or input of energy to activate the solutions.

While a variety of compositions and methods for detecting biofilms have been made and used, it is believed that no one prior to the inventors has made or used an invention as described herein.

BRIEF SUMMARY

Known biofilm-detecting compositions are characterized by relatively high levels of surfactants, particularly high-foaming surfactants. Thus, it may be difficult to apply known biofilm-detecting compositions to large surface areas via a traditional spray nozzle, since the pressure to achieve a desirable spray pattern may entrain too much air in the compositions during spraying. Since known biofilm-detecting compositions rely on entrainment of evolving oxygen generated by the reaction of hydrogen peroxide with enzyme on the test surface, the creation of surface bubbles/foam during spray application has the capability of resembling a positive reaction (i.e., results in "false positives"). The disclosed biofilm-detecting compositions, devices and methods address and overcome these and other problems and provide for effective biofilm monitoring in industries that are sensitive to microbiological contamination and/or infections and outbreaks.

Exemplary aqueous biofilm-detecting composition for use in detecting biofilms on surfaces may comprise radical scavenger, solvent, thickener, hydrogen peroxide, chelating agent, coupling agent and Low-Foaming surfactant. Exemplary compositions may be characterized by few or no false positives when applied to a surface.

Exemplary methods for detecting biofilm on a surface may comprise spraying onto the surface an aqueous biofilm-detecting composition according to the present disclosure, allowing the composition to act for a period of time and visually inspecting the surface for bubbles/foam. Exemplary methods may be characterized by few or no false positives.

Exemplary devices for detecting biofilm on a surface may comprise a biofilm-detecting composition according to the present disclosure that is dispensed from a container through a nozzle. Exemplary devices provide the flexibility to dispense exemplary compositions onto large areas or onto small surface areas (i.e., "spot treat" a surface).

BRIEF DESCRIPTION OF THE DRAWINGS

It is believed the present invention will be better understood from the following description of certain examples taken in conjunction with the accompanying drawing.

The drawing is not intended to be limiting in any way, and it is contemplated that various embodiments of the invention may be carried out in a variety of other ways, including those not necessarily depicted in the drawing. The accompanying drawing that is incorporated in and forms a part of the specification illustrates several aspects of the present invention, and together with the description serves to explain the principles of the invention.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

As used herein, the term "comprising" means that the various components, ingredients, or steps, can be conjointly employed in practicing the present invention. Accordingly, the term "comprising" encompasses the more restrictive terms "consisting essentially of" and "consisting of."

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

All references, including patent applications, patent publications and non-patent literature, that are referred to in the present specification are incorporated by reference herein, unless it is expressly indicated that they are not incorporated by reference herein.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made. The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Known biofilm-detecting compositions are characterized by relatively high levels of surfactant, particularly high-foaming surfactants. Known biofilm-detecting compositions are formulated so that they have sufficient viscosity to cling to surfaces, including vertical surfaces, to which they have been applied. For these and other reasons, it can be difficult to apply known biofilm-detecting compositions to large surface areas via a traditional spray nozzle, since the pressure required to dispense viscous solutions through the nozzle to achieve a desirable spray pattern over a large surface area may result in entrainment of a large amount of air in the compositions during spraying, which may in turn lead to "false positives" as described below.

Since known biofilm-detecting compositions rely on entrainment of evolving oxygen generated by the reaction of hydrogen peroxide with enzyme on the test surface, the creation of surface bubbles/foam during spray application has the capability of resembling a positive reaction. In other words, spraying known compositions can result in "false positives." False positives are undesirable since they may prompt unneeded cleaning/disinfection operations, which may in turn result in delayed operations and increased cost.

Bubbles that are generated by the reaction of catalase with hydrogen peroxide that is present in known biofilm-detecting compositions, tend to remain at the interface between the compositions and the surfaces to which they have been applied. As a result, the bubbles may be difficult for a user to see in a thick composition. Without wishing to be bound by theory, it is believed that the presence of surfactant in biofilm-detecting compositions promotes buoyancy of the bubbles throughout a thick composition. For example, Itram states that "the foaming effect of the surfactant allows a better viewing of the effervescence, as the formed foam contributes to the retention of the bubbles produced by the oxygen released during the reaction."

For at least these reasons, it is surprising to find that the present use of a combination of solvent and coupling agent with low-foaming surfactant addresses and overcomes problems encountered when using known compositions, while providing for: (a) significant extension of stability of viscosity of the present compositions over not only months, but years (as demonstrated in an accelerated shelf life study described herein below); (b) reduction in false positives (being observable in that bubbles generated from shear forces through the nozzle quickly pop, leaving only microbubbles generated from the decomposition of hydrogen peroxide by catalase; and (c) generating microbubbles throughout the thickness of the present compositions and not just at the interface between the exemplary composition and the surface to which it is applied.

The present disclosure is directed to compositions, devices and methods for detecting biofilms, that address and overcome the aforementioned problems.

The present biofilm-detecting compositions may be formulated to have sufficient viscosity such that they may be sprayed over relatively wide surface areas and cling to vertical surfaces. The present compositions may maintain their viscosity for months to years, thus providing for good shelf-stability prior to the first use and between uses.

Additionally, or alternatively, the present compositions are formulated so that bubbles generated by the reaction of hydrogen peroxide with enzyme, e.g., catalase, may be suspended and maintained within the composition, such that they may easily be observed by a user.

Additionally, or alternatively, the present compositions may be formulated to reduce or eliminate false positives that occur when spraying known compositions that contain high levels of surfactant, particularly high-foaming surfactant, through high shear-generating nozzles to achieve broad spray patterns. Without wishing to be bound by theory, it is believed that if surfactant is removed from biofilm-detection compositions altogether, false positives may be eliminated, but radical scavenger present in the compositions may not be solubilized, which may in turn reduce stability of thickening agent, which may negatively impact the viscosity of the compositions. Thus, the present compositions comprise relatively low levels of low-foaming surfactant, in addition to solvent and coupling agent.

Exemplary compositions comprise hydrogen peroxide-containing sprayable liquids that, when in contact with a source of a biofilm enzyme, e.g. catalase, will react to produce oxygen. Oxygen, as it evolves into the composition, may be entrained, creating a white foam in the location of the catalase source. Exemplary compositions may overcome problems associated with the use of known biofilm-detecting compositions, by utilizing solvent and coupling agent (hydrotrope) to solubilize and couple hydrophobic radical scavenger(s) into a predominately aqueous formula. Without wishing to be bound by theory, it is believed that the use of solvent and coupling agent eliminates the need to include ethoxylated alcohol to solubilize radical scavenger(s), thus allowing for the use of much lower foaming surfactants at lower concentrations, than has been previously described.

In some exemplary compositions, low-foaming amine oxide surfactant is included to enhance the positive foaming reaction with enzyme, e.g., catalase, without significantly contributing to false positive bubble formation during spraying.

In some exemplary compositions, wetting agent is added as a leveling agent to increase conformal coverage after spray application.

In some exemplary compositions, a solvent and coupling agent combination may provide for at least two desirable results. First, the combination may make it possible to incorporate surfactant into exemplary compositions, despite the potential of surfactant contributing to false positive bubble/foam formation during spraying. Without wishing to be bound by theory, it is believed that the combination promotes dissipation of extraneous bubbles that are generated during spraying of the exemplary composition. Second, the solvent and coupling agent combination may also provide for a composition that retains its viscosity and hydrogen peroxide concentration over a longer period of time as may be observed in accelerated stability models when compared to known compositions. Exemplary compositions characterized by greater stability may allow for formulation at a lower initial viscosity, contributing to better sprayability, coverage and cling.

These and other advantages of the exemplary compositions, as well as methods of use are described in further detail below.

Exemplary Compositions

Exemplary compositions comprise radical scavenger, solvent, thickener, hydrogen peroxide, chelating agent, coupling agent, low-foaming surfactant and water. Further exemplary compositions may additionally comprise components selected from the group of: colorant, wetting agent, pH adjuster and combinations thereof.

Radical Scavenger

Exemplary compositions comprise one or more radical scavengers. Without wishing to be bound by theory, it is believed that the presence of one or more radical scavengers in exemplary compositions protects against oxidative degradation of polymeric thickener contained therein by participating in a chain-terminating reaction with peroxyl radicals. Phenolic radical scavengers may be uniquely suited to this application, because of their ability to engage in primary antioxidant, radical-scavenging activity without breaking down peroxides.

Radical scavengers of use in exemplary compositions include radical scavengers selected from the general group of: alkyl gallates, hindered phenols, hydroquinone, trihydroxy butyrophenone and combinations thereof.

In reference to the general group of radical scavengers above, alkyl gallates of use may be selected from the group of: ethyl gallate, propyl gallate, octyl gallate, dodecyl gallate and combinations thereof.

In reference to the general group of radical scavengers above, hindered phenols of use may be selected from the group of: butylated hydroxytoluene ("BHT"), butylated hydroxyanisole ("BHA"), tertiary butylhydroquinone ("TBHQ"), tocopherols, tocopherol ester derivatives and combinations thereof. Useful tocopherol ester derivatives may be selected from the group of: tocopheryl acetate, tocopheryl linoleate, tocopheryl nicotinate, tocopheryl succinate and combinations thereof.

In some exemplary compositions, radical scavenger is present in an amount of from about 0.001% to about 0.3%, from about 0.01% to about 0.2%, from about 0.05% to about 0.12% or from 0.08% to about 0.10%.

Solvent

Exemplary compositions comprise one or more solvents. Without wishing to be bound by theory, it is believed that solvent solubilizes the radical scavenger(s) in water. In some exemplary compositions, solvent is at least about 15% soluble in water when measured at 25° C. under atmospheric pressure.

Solvents of use in exemplary compositions may be selected from the general group of: glycol ethers, glycol ether acetates, glycol diethers (glymes) and combinations thereof.

In reference to the general group of solvents above, glycol ethers of use may be selected from the group of: ethylene glycol propyl ether, ethylene glycol n-butyl ether, diethylene glycol methyl ether, diethylene glycol n-butyl ether, diethylene glycol ethyl ether, triethylene glycol methyl ether, triethylene glycol ethyl ether, triethylene glycol n-butyl ether, propylene glycol methyl ether, propylene glycol n-propyl ether, dipropylene glycol methyl ether, dipropylene glycol n-propyl ether, tripropylene glycol methyl ether, and polyethylene glycol phenyl ether; glycol ether acetates, such as propylene glycol methyl ether acetate and dipropylene glycol methyl ether acetate; and glycol diethers (glymes), such as ethylene glycol dimethyl ether, ethylene glycol diethyl ether, diethylene glycol dimethyl ether, diethylene glycol diethyl ether, triethylene glycol dimethyl ether, tetraethylene glycol dimethyl ether, dipropylene glycol dimethyl ether, poly(ethylene glycol) dimethyl ether and combinations thereof.

In some exemplary compositions, solvent is selected from the group of: ethylene glycol propyl ether, ethylene glycol n-butyl ether, diethylene glycol methyl ether, diethylene glycol n-butyl ether, diethylene glycol ethyl ether, triethylene glycol methyl ether; and glycol diethers (glymes), such as ethylene glycol dimethyl ether, ethylene glycol diethyl ether, diethylene glycol dimethyl ether, diethylene glycol diethyl ether, dipropylene glycol dimethyl ether and combinations thereof.

In some exemplary compositions, solvent is selected from the group of: ethylene glycol propyl ether, ethylene glycol n-butyl ether, diethylene glycol methyl ether, diethylene glycol n-butyl ether, diethylene glycol ethyl ether and combinations thereof.

In some exemplary compositions, the solvent is selected from glycol ethers, such as ethylene glycol propyl ether, ethylene glycol n-butyl ether, diethylene glycol methyl ether, diethylene glycol n-butyl ether, diethylene glycol ethyl ether; and combinations thereof.

In some exemplary compositions, solvent is present in an amount of from about 5% to about 22%, from about 5% to about 15%, from about 8% to about 19% or from about 12% to about 15%.

Thickener

Exemplary compositions comprise one or more thickeners. Without wishing to be bound by theory, it is believed that thickener allows the composition to be formulated as a sprayable liquid that once sprayed, may cling to various surfaces, including vertical surfaces. By clinging to the surface, the composition and any resulting bubbles/foam may be held in place at their origin, rather than dislocating to another area, such as by running down a vertical surface, thus making it difficult to pinpoint where the detected biofilm is located. Thus, the use of thickener in exemplary compositions, can be advantageous since it holds the compositions and/or any bubbles/foam in place long enough to identify the locus of a biofilm. The locus of the biofilm may be used interchangeably with the terms "harborage site," "niche" or "nidus."

Thickeners of use in exemplary compositions may be selected from the group of: natural gums (such as xanthan gum, guar gum, and gellan gum), alginates (such as sodium alginate, potassium alginate, propylene glycol alginate, and ammonium alginate), cellulosic thickeners (such as carboxymethylcellulose and its sodium salt, hydroxyethyl cellulose, and hydroxypropyl methylcellulose), organic polymeric acid colloids (such as polyuronic acids, carboxypolymethylene compounds, polyester resins containing free carboxyl groups (such as partially hydrolyzed polyacrylates or polymethacrylates, polyacrylic acid, polymethacrylic acid, copolymers of unsaturated esters and acids (such as copolymers of methylmethacrylate and methacrylic acid and copolymers of acrylic acid crosslinked with polyallyl sucrose))), clays (such as montmorillonite, kaolin, illite, saponite, bentonite, hectorite, beidellite, stevensite, attapulgite, sepiolite, laponite), hydrophobically modified fumed silicas and combinations thereof.

In some exemplary compositions, thickener is selected from the group of: natural gums (such as xanthan gum, guar gum, and gellan gum), organic polymeric acid colloids (such as polyester resins containing free carboxyl groups (such as partially hydrolyzed polyacrylates or polymethacrylates, polyacrylic acid, polymethacrylic acid, copolymers of unsaturated esters and acids (such as copolymers of methylmethacrylate and methacrylic acid and copolymers of acrylic acid crosslinked with polyallyl sucrose))), hydrophobically modified fumed silicas and combinations thereof.

In some exemplary compositions, thickener is selected from the group of: natural gums (such as xanthan gum and guar gum), organic polymeric acid colloids (such as copolymers of unsaturated esters and acids (such as copolymers of methylmethacrylate and methacrylic acid and copolymers of acrylic acid crosslinked with polyallyl sucrose))) and combinations thereof.

In some exemplary compositions, thickener is present in the amount of from about 0.1% to about 1% by weight, from about 0.1% to about 0.65%, from about 0.2% to about 0.8% or from about 0.3% to about 0.6%.

Hydrogen Peroxide

Exemplary compositions comprise hydrogen peroxide. Hydrogen peroxide reacts with enzyme(s), e.g. catalase, that are present in a biofilm. The reaction of the hydrogen peroxide with the enzyme(s), e.g. catalase, produces bubbles, and ultimately, foam. The presence of bubbles and/or foam on the tested surface provides a visual indication of the presence of biofilm on the tested surface.

In some exemplary compositions, hydrogen peroxide is present in an amount of from about 1% to about 10%, from about 2% to about 9%, from about 3% to about 8%, from about 4.5% to about 6.5% or from about 5% to about 6.5% by weight.

Air bubbles caused by entrainment of air during application may be exponentially larger than bubbles caused by the evolution of oxygen from the reaction of hydrogen peroxide with catalase. Because of the random nature of air entrainment, the volume and density of entrained air bubbles that result from spraying via cavitation through the spray mechanism itself and/or via capture of air present between the application substrate and the composition upon adherence, may be unevenly distributed and innately large. On the other hand, bubbles created by the decomposition of hydrogen peroxide by catalase may form a rapid but steady evolution of diatomic oxygen from a multitude of reaction sites, providing just as many points for nucleation to occur. The incorporation of surfactants may reduce surface tension, coalescence time and mass transfer across interfaces, thus reducing the size of the bubbles while increasing stability. Moreover, because of the localized origin of the reaction of hydrogen peroxide with catalase, the resulting bubbles may form a dense collection of bubbles that scatters light very effectively and gives it a white appearance (noting that is the principal behind why foam is white). In contrast, a large volume of low-density bubbles caused by spray application, may not result in a dense collection of bubbles, and as such may appear comparatively less white.

Chelating Agent

Exemplary compositions comprise one or more chelating agent(s). Without wishing to be bound by theory, it is believed that by binding metal ions that are present in the exemplary compositions, the chelating agent stabilizes the compositions. For example, it is believed that chelating agent prevents decomposition of hydrogen peroxide by sequestering the metal ions that would otherwise catalyze its decomposition in the exemplary compositions. Chelating agents of use in exemplary compositions include those selected from the group of: phosphonic acid, phosphonic acid salts, polyamino phosphonic acid, polyamino phosphonic acid and salts thereof.

In some exemplary compositions, chelating agents are selected from the group of: phosphonic and polyamino phosphonic acids (such as 1-hydroxyethilidene 1,1-diphosphonic acid, aminotris (methylene phosphonic acid), diethylenetriamine penta(methylene phosphonic acid), bis(hexamethylene triamine penta(methylenephosphonic acid)), ethylidenediamine tris(methylene phosphonic acid), hexamethylenediamine tetra(methylene phosphonic acid), and their potassium and sodium salts), water soluble alkali metal stannates (such as sodium stannate) and combinations thereof.

In some exemplary compositions, chelating agents are selected from the group of:
phosphonic and polyamino phosphonic acids (such as 1-hydroxyethilidene 1,1-diphosphonic acid, aminotris (methylene phosphonic acid), diethylenetriamine penta(methylene phosphonic acid), ethylidenediamine tris(methylene phosphonic acid), and their potassium and sodium salts) and combinations thereof.

In some exemplary compositions, chelating agents are selected from the group of: phosphonic and polyamino phosphonic acids (such as 1-hydroxyethilidene 1,1-diphosphonic acid, -hydroxyethilidene 1,1-diphosphonic acid, dipotassium salt, diethylenetriamine penta(methylene phosphonic acid), sodium salt, and combinations thereof.

In some exemplary compositions, chelating agent is present in the amount of from about 0.01% to about 0.1%, from about 0.03% to about 0.09% or from about 0.05% to about 0.07%.

Coupling Agent

Exemplary compositions comprise one or more coupling agents. Benefits of utilizing coupling agents in combination with solvent in exemplary compositions are described above. Without wishing to be bound by theory, it is believed that the presence of coupling agent in the present compositions improves the solubility of the radical scavenger.

Coupling agents of use in exemplary compositions include those selected from the group of: sodium, potassium and ammonium salts of alkyl aryl sulfonates (such as xylene sulfonate, toluene sulfonate and cumene sulfonate) and combinations thereof.

In some exemplary compositions, the coupling agent is selected from the group of: sodium and potassium salts of alkyl aryl sulfonates (such as xylene sulfonate, toluene sulfonate, and cumene sulfonate) and combinations thereof.

In some exemplary compositions, the coupling agent is selected from the group of: sodium and potassium salts of xylene sulfonate and cumene sulfonate and combinations thereof.

In some exemplary compositions, the coupling agent is selected from the group of: sodium xylene sulfonate and sodium cumene sulfonate and combinations thereof.

In some exemplary compositions, the coupling agent is present in an amount of from about 1% to about 10%, from about 2% to about 8%, from about 2% to about 7%, from about 3% to about 8%, from about 3% to about 7%, from about 4% to about 8% or from about 4% to about 7% by weight.

Low-Foaming Surfactant

Exemplary compositions comprise one or more low-foaming surfactants. The term "low-foaming" as used herein in relation to surfactants encompasses "ultra-low foaming" surfactants. Low-foaming surfactants are best suited for use in exemplary compositions. As used herein, "low-foaming" means that very little or no foam is generated by the surfactant when agitated, for example via shear forces resulting from spraying through a nozzle. Further, any foam which is generated is typically unstable and rapidly breaks down, thus preventing accumulation of foam during the process. These types of "low-foaming" surfactants are to be contrasted with so-called "high-foaming" systems in which copious amounts of foam are generated and the foam remains stable for a long period of time.

Without wishing to be bound by theory, it is believed that the presence of low-foaming surfactant in the exemplary compositions increases foaming volume and stability during the reaction of hydrogen peroxide with catalase, while keeping excess bubbling/foaming to a minimum when the composition is applied by spraying, thus resulting in reduced false positives.

Low-foaming surfactants of use in exemplary compositions may be broken into two categories: low-foaming amine oxides and low-foaming non-amine oxide surfactants. Some exemplary compositions may comprise only low-foaming amine oxides. Some exemplary compositions may only comprise low-foaming non-amine oxide surfactants. Some exemplary compositions may comprise a combination of low-foaming amine oxides and low-foaming non-amine oxide surfactants.

"Low-foaming surfactant" as used herein means surfactant that is characterized by: (a) a hydrophobic-lipophilic balance (HLB) of from about 6 to about 13, or from about 6 to less than 10, or from about 7 to about 10, or from about 7 to about 9; and/or (b) a Ross-Miles Initial Foam Height of greater than 0 and up to about 5 cm, or from about 0.1 cm to about 5 cm, from about 0.2 to about 4 cm, or from about 0.3 cm to about 3 cm, or from about 0.6 cm to about 2 cm, when the surfactant is measured at 1 weight percent of active surfactant in DI water at 25° C. using ASTM D1173-53-Standard Test Method for Foaming Properties of Surface-Active Agents. It should be noted that some low-foaming surfactants of use in exemplary compositions may have an HLB greater than 10, so long as they have a Ross-Miles Initial Foam Height of from about 0.2 cm to about 5 cm, from about 0.3 to about 4 cm, or from about 0.5 cm to about 3 cm, or from about 0.6 cm to about 2 cm.

"High-foaming surfactant" as used therein means surfactant that is characterized by: (a) an HLB of greater than 10; and/or (b) a Ross-Miles Initial Foam Height of greater than 5 cm. Some exemplary compositions may be substantially free of high-foaming surfactant, i.e., they may contain less than about 3 wt %, less than about 2 wt %, less than about 1 wt %, less than about 0.5 wt %, less than about 0.01 wt % or even completely free (i.e., 0 wt %) of high-foaming surfactant.

Low-Foaming Amine Oxides

Amine oxides are added to a wide variety of compositions to act as foaming agents, foam enhancers and/or foam stabilizers. For example, because of these foam-generating characteristics, amine oxides are typically found in shampoos, bath preparations and hand dish detergents. Two broad classes of amine oxides typically used in the aforementioned applications include dimethyl alkyl amine oxides and bis(2-hydroxyethyl) alkyl amine oxides. These amine oxides are thought of as medium to high-foaming surfactants, which contribute to the overall foamability and foam stability of the detergents and cleaning compositions.

Alkoxylated amine oxides are another group of amine oxides understood to be high-foaming. For example, U.S. Pat. No. 3,449,431 (Swenson) repeatedly characterizes certain alkoxylated amine oxides as suds builders and not as low foaming surfactants. Such molecules would likely be unsatisfactory for exemplary compositions described herein.

In some exemplary compositions, the amine oxide constituent includes at least one amine oxide having a structure according to Formula I:

Formula I

Wherein $R_1$ is selected from an alkyl group having from 6 to 22 carbon atoms, or a substituted aryl group having from 7 to 22 carbon atoms; $R_2$ comprises from 0 to 7 moles of alkoxylated units; and $R_3$ and $R_4$ are each at least one alkoxylated unit, wherein the total number of alkoxylated units present in $R_3$ and $R_4$ is from 2 to 30.

As used throughout the specification and claims, terms such as "between 6 and 22 carbon atoms," "between 7 and 22 carbon atoms" and "C6-C18" are used to designate carbon atom chains of varying lengths and to indicate that various conformations are acceptable including branched, cyclic and linear. The terms further designate that various degrees of saturation are acceptable. It should also be understood that the amine oxides of use in exemplary compositions may be isolated or present within a mixture and remain within the scope of the invention. Alkoxylated units refer to the individual alkylene oxide units added to the amine. Typically, this means ethyleneoxy, propyleneoxy and butyleneoxy, including isomers.

Exemplary amine oxides of use comprise the following:

Alkoxylated units for $R_2$ are selected from the group of: ethyleneoxy, propyleneoxy and butyleneoxy and mixtures thereof. It should be noted, however, that variation at the $R_2$ position is intended and that other alkoxylated units, such as styrene oxide, are within the scope of the invention.

Alkoxylated units for $R_3$ and $R_4$ are selected from the group of: ethyleneoxy, propyleneoxy, butyleneoxy units including mixtures. For some exemplary amine oxides of use, $R_3$ and $R_4$ are each comprised of ethyleneoxy units.

Some exemplary amine oxides of use include from about 2 to about 20 moles of alkoxylated units present in $R_3$ and $R_4$. For some exemplary amine oxides of use, $R_3$ and $R_4$ include from about 2 to about 15 moles of alkoxylated units.

For some exemplary amine oxides of use, the amine oxide constituent includes amine oxides having an ether linkage and no alkoxylated units in $R_2$ according to Formula I in the hydrophobe. These exemplary amine oxides have a structure according to Formula II:

Formula II

Wherein, $R_1$ is selected from an alkyl group having between 6 and 22 carbon atoms, or a substituted aryl group having between 7 and 22 carbon atoms; $R_3$ and $R_4$ are each at least one alkoxylated unit and the total number of alkoxylated units present in $R_3$ and $R_4$ is from 2 to 30. For some exemplary amine oxides, $R_3$ and $R_4$ are each alkoxylated units selected from ethyleneoxy, and propyleneoxy (including mixtures) and that from about 2 to about 10 moles of such alkoxylated units are included.

Some exemplary amine oxides may have the structure according to Formula II, wherein $R_1$ is an iso-branched alkyl group having from 9 to 11 carbon atoms, and $R_3$ and $R_4$ are each alkoxylated units selected from ethyleneoxy groups, propyleneoxy groups and mixtures thereof. Useful mixtures of these exemplary amine oxides may comprise $R_1$ groups that are iso-branched alkyl chain groups with the predominant chain length being 10 carbon atoms and wherein from about 2 to about 10 moles of the alkoxylated units of $R_3$ and $R_4$ are present in the mixture.

Low-Foaming Non-Amine Oxide Surfactants

Exemplary low-foaming non-amine oxide surfactants ("NAOS") of use in the present invention include the following surfactants.

Useful low-foaming NAOS include, but are not limited to, those selected from the group of: diphenyl sulfonate derivatives (e.g., alkyl diphenyloxide disulphonates), fatty acid sulfonates, phosphate esters, alcohol alkoxylates (e.g., end-capped alcohol alkoxylates), ethylene oxide/propylene oxide block copolymers, alkyl ether carboxylic acids, alkyl polyglycosides, alkylphenol alkoxylates, alkanoate salts and mixtures thereof.

As noted above, exemplary compositions may comprise low-foaming amine oxide, NAO and combinations thereof, thus making up the "total surfactant" in the compositions. Exemplary compositions may comprise from about 0.1% to about 3%, from about 0.3% to about 1.5% or from about 0.7% to about 1% total surfactant.

Some exemplary compositions may comprise surfactants selected from the group of: low-foaming linear amine oxide, low-foaming branched amine oxide, alcohol alkoxylates (e.g., end-capped alcohol alkoxylates), alkyl polyglycosides, alkanoate salts and combinations thereof.

Some exemplary compositions may comprise surfactants selected from the group of: low-foaming linear amine oxide, low-foaming branded amine oxide and combinations thereof.

Water

Exemplary compositions comprise water. In exemplary compositions water brings the balance of total ingredients up to 100%.

Colorant

Exemplary compositions may comprise one or more colorants. Inclusion of colorant in the present compositions may provide a visual contrast to white bubbles/foam that is generated when the composition reacts with enzyme present in biofilm. Thus, the use of colorant in exemplary compositions may make it easier for a user to determine whether a positive test for biofilm has occurred.

Colorants of use in exemplary compositions may be selected from the group of: anionic dyes, nonionic dyes, anionic pigments, nonionic pigments and combinations thereof.

In some exemplary compositions, colorant is selected from the group of: azo dyes, anthraquinone-based colorants and combinations thereof.

In some exemplary compositions, the colorant is anthraquinone dye.

In some exemplary compositions, the colorant may have a hue that is red, blue or purple.

In some exemplary compositions, colorant is present in the amount of about 0.005% to about 0.2% by weight, such as about 0.005% to about 0.15% by weight, about 0.01% to about 0.2% by weight, about 0.01% to about 0.15% by weight, about 0.025% to about 0.2% by weight, about 0.025% to about 0.15% by weight, and about 0.025% to about 0.12% by weight.

Wetting Agent

In addition to the components described above, some exemplary compositions may further comprise one or more wetting agents. Without wishing to be bound by theory, it is believed the presence of wetting agent in exemplary compositions modifies the surface tension of the composition to increase spreading and/or wetting of the composition on the surfaces to which it applied, without substantially promoting foaming performance.

Wetting agents of use may be selected from the group of: polyethylene glycols having a molecular weight between from about 20 to about 2,000, from about 100 to about 1,000 or from about 200 to about 500 Daltons, EO/PO block copolymers, alkyl sulfosuccinates and their salts, and combinations thereof.

In some exemplary compositions, wetting agent is selected from the group of: polyethylene glycols having a molecular weight between about 200 and 500 Daltons, alkyl sulfosuccinates and their salts, and combinations thereof.

In some exemplary compositions, wetting agent is selected from having a molecular weight between about 200 and 500 Daltons) and combinations thereof.

In some exemplary compositions, wetting agent is present in the amount of from about 0.1% to about 5%, from about 0.1% to about 3%, from about 0.4% to about 5%, from about 0.4% to about 3%, from about 0.1% to about 1.5%, from about 0.8% to about 5%, from about 0.8% to about 3% or from about 0.8% to about 1.5% by weight.

pH Adjuster

Exemplary compositions have a pH of from about 3 to about 7, from about 3 to less than 6.0, from about 3.5 to about 6.5, from about 4 to about 6 or from about 4.5 to about 5.5. The pH of exemplary compositions may be adjusted using acid, base and combinations thereof.

Exemplary acid pH adjusters may be selected from the group of: formic acid, acetic acid, lactic acid, citric acid, glycolic acid, sulfamic acid, phosphoric acid and combinations thereof.

Exemplary acid pH adjusters may be selected from the group of: sodium hydroxide, potassium hydroxide, ammonium hydroxide, ammonia, amines, ethanolamine, diethanolamine, triethanolamine, aminomethyl propanol, aminomethyl propanediol, diisopropanolamine and combinations thereof.

Exemplary compositions may comprise pH adjuster selected from the group of: acetic acid, lactic acid, citric acid, glycolic acid, sodium hydroxide, potassium hydroxide, ammonium hydroxide and combinations thereof.

Exemplary compositions may comprise pH adjuster selected from the group of: lactic acid, citric acid, sodium hydroxide, potassium hydroxide and combinations thereof.

Exemplary compositions may comprise pH adjuster in an amount of from about 0.001% to about 0.5%, from about 0.01% to about 0.5%, from about 0.01% to about 0.2%, from about 0.01% to about 0.1%, from about 0.04% to about 0.2%, from about 0.055% to about 0.2%, from about 0.04% to about 0.1% or from about 0.055% to about 0.1%.

Devices

Exemplary compositions may be applied onto a surface in order to detect biofilm using any suitable method that delivers a fan of liquid droplets without creating a significant amount, or any, false positives. Exemplary devices for use in applying exemplary compositions comprise a spray nozzle and containing an exemplary composition, wherein the devices are configured so that the exemplary composition is dispensed through the spray nozzle over wide surface areas, while still providing the flexibility to dispense exemplary composition onto small surface areas (i.e., "spot treat" a surface).

The geometry of a spray nozzle of a device may determine how a composition contained therein is applied, such as for example, via a single stream or fan of liquid droplets. Spraying a fan of liquid droplets may result in application of a composition onto a larger surface area than would otherwise be achieved by spraying the same composition in a single stream.

Exemplary devices comprise a nozzle for applying the exemplary compositions to a surface, via a fan of liquid droplets using a spray angle of from about 70 degrees to about 110 degrees, from about 70 degrees to about 100 degrees, from about 70 degrees to about 90 degrees, from about 70 degrees to about 80 degrees, from about 80 degrees to about 90 degrees or at about 80 degrees.

In some exemplary devices, a nozzle may deliver the exemplary compositions to a target surface at a flow rate of from about 0.1 to about 0.20 or from about 0.1 to about 0.15 gallons per minute using spray pressure of from about 40 to about 50 pounds per square inch ("PSI"), from about 30 to about 55 PSI or from about 20 to about 60 PSI. In use, some exemplary devices may be from about 12 inches, from about 10 inches or from about 8 inches away from the surface to be sprayed.

When the exemplary compositions are sprayed as a fan of liquid droplets to a broad surface, there may be little to no false positives due to the spraying action. Exemplary compositions are typically sprayed using a wide spray angle as noted above to produce a fan of liquid droplets that cover a large surface area.

Exemplary nozzles of use to dispense exemplary compositions with little to no bubbling/foaming due to high shear conditions that may promote entrainment of air in the solution, thereby causing false positive bubbling/foaming to occur include nozzles sold by Sprayer Depot (Orlando, Fla.), Pentair (Minneapolis, Minn.), TeeJet Technologies (Glendale Heights, Ill.) and Spraying Systems Co. (Wheaton, Ill.). Some exemplary devices comprise the Hypro F80-01 flat fan spray tip available from Sprayer Depot.

Methods for Detecting Biofilm

Exemplary methods for detecting biofilm on a surface are described below.

Exemplary methods are characterized by low to no false positives, such as for example, bubbles/foam being generated by dispensing a composition containing high-foaming surfactants through a nozzle.

An exemplary method for detecting biofilm on a surface, wherein the method is characterized by low to no false positives, the method comprising:

(i) spraying onto a surface a composition according to the present disclosure;

(ii) allowing the composition to act for a period of time; and (iii) visually inspecting the surface for bubbles/foam.

The spraying action required in (i) refers to an action of applying a thin layer of the composition on the surface, to which end a spray device as described herein can be used. Use of a spray device as described herein to spray exemplary compositions may result in a method that is not characterized by false positives, i.e., significant and/or sustained bubbling/foaming of a composition as of being dispensed through a nozzle. Exemplary compositions may be sprayed onto a surface from any suitable distance. In some exemplary methods, the spraying in (i) comprises spraying an exemplary composition on a surface to be tested, wherein spraying is from a minimum distance of from about 12 inches, from about 10 inches or from about 8 inches, spraying onto a surface a composition according to the present disclosure in a side-to-side motion. In some exemplary methods, allowing the composition to act per (ii) can occur up to two minutes or less. In some exemplary methods (ii) and (iii) can be undertaken simultaneously or during overlapping sequences of time. In some exemplary methods, visualization per (iii) comprises visually inspecting the surface within two minutes of application of the exemplary composition. In some exemplary methods, the methods further comprise (iv) rinsing the surface with water after (iii).

An appearance of bubbles is indicative of an enzymatic reaction of enzyme, e.g., catalase, that is present in a biofilm, and therefore allows detection of a biofilm's presence on the surface by means of a simple visual inspection. An appearance of bubbles may occur immediately upon application of exemplary compositions.

The simplicity of the exemplary methods has the advantage of allowing its application in situ for detecting biofilms on any surface, in medical and industrial facilities as well as in the domestic environment and allows fast and efficient detection of biofilms.

Like the method described in EP 2902497A (Itram Higiene, S.L.), which is incorporated herein by reference, the exemplary methods allow for the detection of both mono- and multi-species biofilms, particularly those that are catalase-positive. Examples of microorganisms that have some type of catalase are, for example, within the bacterial genus, *Salmonella, Listeria, Escherichia, Staphylococcus, Micrococcus, Helicobacter, Enterococcus, Proteus, Pseudomonas*, among others; and within the fungal genus, *Saccharomyces, Candida, Aspergillus, Fusarium, Botrytis, Cladosporium*, among others, as described in the article Beltran-Garcia et al., *Catalasas de hongos fitopatogenos: Factores de virulencia y resistencia a los fungicidal*?, Rev. Mex. Fitopatol., 2006, 24(1), 50-58.

In practice, the exemplary methods are suitable for the detection of virtually all the biofilms usually present in the medical, industrial and household environments, since generally they always include one bacterium that is catalase-positive. Since most environmental biofilms are of the multispecies type, it may be sufficient that the biofilm comprises at least one catalase-positive species to be reactive to the detection method.

As for the surface, virtually any type of surface is suitable for the biofilm detection method of the present invention to be applied, including but not limited to, surfaces made from one or more of metallic surfaces, such as aluminum, steel, or stainless steel; or surfaces such as glass, ceramic or porcelain, plastic surfaces, such as thermoplastic or thermosetting polymers, for example, epoxy resins, among other possible materials. Surfaces that are suitable for exemplary biofilm detection methods may be selected from the following group: Al 1100, Al 5052, Al 3003, stainless steel, carbon steel, SS 304, SS 316, HDPE, LDPE, polypropylene, PVC, PTFE, Acetyl, polycarbonate, mylar, Viton, BUNA-N and combinations thereof.

Surfaces to be tested may be in any physical disposition, including but not limited to, horizontal, vertical and combinations thereof, and may include cracks and/or crevasses, which may be hard to clean.

Exemplary methods for the detecting biofilm may be particularly advantageous as an assistant for the establishment of the Critical Control Points (CCP) in the surfaces of the agri-food industry.

EXAMPLES AND DATA

Exemplary compositions A through I are set forth in TABLE 1. Comparative compositions J through S are set forth in TABLE 2.

appropriate for the final composition. The following are added sequentially to the mixing vessel, while mixing: chelating agent (if present in the composition), hydrogen peroxide, radical scavenger in ethoxylated fatty alcohol (if radical scavenger is present in the composition, otherwise just ethoxylated fatty alcohol without radical scavenger), alkyl ether sulfate (if present in the composition), and colorant (if present in the composition). The resulting composition is pH-adjusted to a desired value using an appropriate acid or base if needed.

Comparative composition S is made as follows. DI water is charged to a mixing vessel and thickening agent is slowly dispersed into the DI water while mixing. Chelating agent is added, followed by hydrogen peroxide and amine oxide surfactant. Finally, pH is adjusted to 7.5 using an appropriate acid or base if needed.

TABLE 1

| | Example A | Example B | Example C | Example D | Example E | Example F | Example G | Example H | Example I |
|---|---|---|---|---|---|---|---|---|---|
| Radical Scavenger | 0.090 | 0.090 | 0.050 | 0.300 | 0.100 | 0.100 | 0.100 | 0.100 | 0.400 |
| Solvent | 13.00 | 13.00 | 13.00 | 22.00 | 10.00 | 10.00 | 12.00 | 14.00 | 8.00 |
| Thickener | 0.45 | 0.36 | 0.55 | 1.00 | 0.50 | 0.50 | 0.60 | 1.00 | 0.50 |
| Hydrogen peroxide | 6.00 | 6.00 | 7.50 | 10.00 | 7.00 | 5.50 | 7.50 | 3.00 | 6.00 |
| Chelating agent | 0.070 | 0.070 | 0.070 | 0.100 | 0.050 | 0.010 | 0.100 | 0.080 | 0.070 |
| Low Foaming Surfactant | 0.80 | 0.80 | 1.50 | 3.00 | 0.40 | 0.50 | 1.50 | 0.50 | 0.75 |
| Colorant | 0.035 | 0.035 | 0.005 | 0.200 | 0.025 | 0.050 | 0.050 | 0.075 | 0.100 |
| Coupling Agent | 4.50 | 4.50 | 4.50 | 1.00 | 10.00 | 3.00 | 2.10 | 1.50 | 5.00 |
| Wetting Agent | 1.40 | 1.40 | 0.50 | — | 5.00 | 0.10 | 2.50 | 2.20 | 0.20 |
| pH range | q.s. water 4.5-5.5 | q.s. water 4.5-5.5 | q.s. water 4.5-5.5 | q.s. water 3.0-4.0 | q.s. water 4.0-5.0 | q.s. water 6.0-7.0 | q.s. water 4.0-5.0 | q.s. water 6.0-7.0 | q.s. water 4.0-5.0 |

TABLE 2

| | Example J | Example K | Example L | Example M | Example N | Example O | Example P | Example Q | Example R | Example S |
|---|---|---|---|---|---|---|---|---|---|---|
| Radical Scavenger | 0.100 | — | — | 0.100 | 0.100 | 0.100 | 0.100 | 0.100 | 0.100 | — |
| Solvent | — | — | — | — | — | — | — | — | — | — |
| Thickener | 0.54 | 0.62 | 0.66 | 0.10 | 0.15 | 0.20 | 0.25 | 1.00 | 1.50 | 0.40 |
| Hydrogen peroxide | 5.50 | 5.50 | 5.50 | 0.50 | 1.00 | 3.00 | 5.00 | 10.00 | 15.00 | 3.00 |
| Chelating agent | 0.063 | — | 0.125 | — | 0.025 | 0.050 | 0.200 | 3.000 | 5.000 | 0.800 |
| Total Surfactant | 8.40 | 8.50 | 8.50 | 15.00 | 15.00 | 13.00 | 10.00 | 15.00 | 15.00 | 0.90 |
| Alkyldimethylamine oxide | — | — | — | — | — | — | — | — | — | 0.90 |
| Ethoxylated Fatty Alcohol | 4.90 | 5.00 | 5.00 | 1.00 | 5.00 | 5.00 | 7.00 | 10.00 | 14.00 | — |
| Alkyl Ether Sulfate | 3.50 | 3.50 | 3.50 | 14.00 | 10.00 | 8.00 | 3.00 | 5.00 | 1.00 | — |
| Colorant | 0.025 | 0.025 | 0.025 | — | 0.0001 | 0.001 | 0.010 | 0.050 | 0.100 | — |
| Coupling Agent | — | — | — | — | — | — | — | — | — | — |
| Wetting Agent | — | — | — | — | — | — | — | — | — | — |
| pH range | q.s. water 4.0-5.0 | q.s. water 4.5-5.5 | q.s. water 5.0 | q.s. water | q.s. water | q.s. water | q.s. water | q.s. water | q.s. water | q.s. water 7.5 |

Exemplary compositions A through I are made as follows. Solvent is charged to a mixing vessel and radical scavenger dissolved into the solvent under mixing. Wetting agent, if present in the composition, is added, followed by thickener to generate a slurry. DI water is added, followed by chelating agent, hydrogen peroxide, low foaming surfactant, coupling agent and colorant. The composition is adjusted to a final pH using an appropriate acid or base.

Comparative compositions J through R are made as follows. Radical scavenger, if present in the composition, is pre-dissolved in ethoxylated fatty alcohol. DI water is charged to a mixing vessel and the thickening agent is dispersed under mixing. If the thickener present in the composition is alkali swellable, a suitable base is added in a sufficient amount to achieve the final pH and viscosity Accelerated stability testing of exemplary and comparative compositions is conducted for Examples A, B, C, J, K and L at 50° C. in a stability chamber. A sample of each composition to be tested is contained in a 4 fl. oz. brown HDPE (high-density polyethylene), wide-mouth bottle. A minimum of 2 samples (N=2) (Preferably 3) is placed into each stability chamber.

Initial measurements of % peroxide, viscosity and pH are performed for each sample, prior to the sample being placed in the stability chamber. % peroxide, viscosity, pH and bubbling reaction are evaluated over time, noting that samples are pulled out of the stability chamber to equilibrate to room temperature before measuring viscosity, pH and % hydrogen peroxide.

Viscosity is measured in centipoise using a Brookfield DVE Viscometer at 23-25° C. with an LV-3 spindle at 20 RPM.

% peroxide is measured by titration using ceric sulfate with ferroin indicator.

pH is measured using a Thermo Scientific Orion 2 Star pH meter with a Thermo Scientific Sure-Flow Combination pH Glass Body Electrode.

For accelerated stability results, the appropriate conversion of elevated temperature/time duration is calculated using the 10-degree rule for predicting shelf-life. According to this rule, the rate of a chemical reaction will increase by a factor $Q_{10}$ for every 10° C. increase in temperature. Typically, $Q_{10}=2$, i.e., a doubling of the reaction rate for each 10° C. increase in the temperature above the use or storage temperature.

For any accelerated aging and ambient temperatures selected, the relationship of environmental test time to shelf-life time is:

$$\text{Time}_{T1}=\text{Time}_{RT}/Q_{10}^{(T_1-T_{RT})/10)}, \text{ where } T_1=\text{oven aging temperature}, T_{RT}=\text{room temperature (ambient/use/storage)}, \text{ and } Q_{10}=\text{reaction-rate coefficient}.$$

Figure 1:
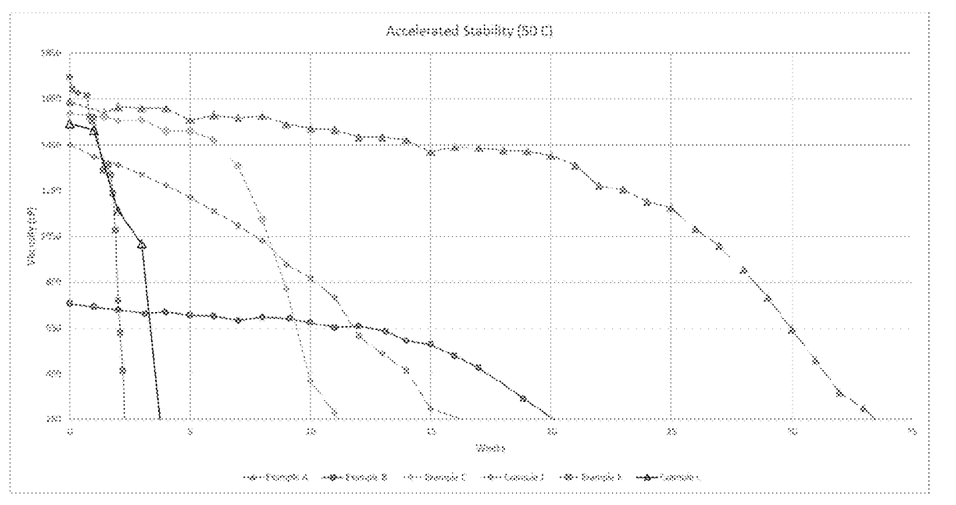
FIG. 1 depicts a plot of viscosity over time of exemplary and comparative compositions that are subject to accelerated stability testing.

In reference to exemplary composition A as shown in FIG. 1, the following shelf life can be expected using the $Q_{10}$ rule, based upon the number of weeks that the viscosity of composition A remains above 500 cP, noting that after the viscosity of a composition falls below 500 cP, it may become too runny for a commercialized composition that is to be applied to vertical surfaces, among others:

31 weeks=)Time$RT$/2(50°-25°)/10=Time$RT$/22.5=Time$RT$/5.66

Time$RT$=31×5.66=175.46 weeks or

Time$RT$=175.56 weeks×(1 year/52 weeks)=3.37+ years

In reference to exemplary composition B as shown in FIG. 1, the following shelf life can be expected using the Q10 rule, based upon the number of weeks that the viscosity of composition B remains above 500 cP, noting that after the viscosity of a composition falls below 500 cP, it may become too runny for a commercialized composition that is to be applied to vertical surfaces, among others:

16 weeks=)Time$RT$/2(50°-25°)/10=Time$RT$/22.5=Time$RT$/5.66

Time$RT$=16×5.66=90.56 weeks or

Time$RT$=90.56 weeks×(1 year/52 weeks)=1.74+years

There were no changes in the hydrogen peroxide or pH levels during the periods tested. Therefore, changes in viscosity levels were used to monitor stability of the compositions. As described below, conversion of accelerated viscosity data to real time suggests that exemplary compositions will be stable for months to years.

A plot of viscosity as it changes over time is set forth in FIG. 1 for Examples A, B, C, J, K and L. The resulting curves may be construed to demonstrate the following.

Referencing the stability data for exemplary composition B, this composition shows that when holding amounts of all other components constant in comparison to exemplary composition A, a reduction in the thickening agent in exemplary composition B still maintains a level of stability that is better than the comparative example J, which contains similar levels of radical scavenger and chelating agent.

Exemplary composition C when compared to exemplary composition A, may demonstrate the impact on stability of an exemplary composition comprising comparatively less radical scavenger. Accelerated stability data for Example C demonstrates a marked decrease in viscosity stability compared to Example A. Since the amount of thickener, solvent, and coupling agent is similar between the two compositions, it is believed that the decrease in viscosity stability may be due to the lower concentration of radical scavenger in Example C compared to Example A.

Comparative composition J when compared to exemplary compositions A or B, may demonstrate that markedly improved stability of a composition is achieved when radical scavenger is incorporated in the composition through a combination of solvent and coupling agent, per exemplary compositions A and B, versus incorporation via dissolution into ethoxylated alcohol, per comparative example J. Comparative example J when compared to comparative examples K and L, may demonstrate that the presence of radical scavenger in a composition per comparative example J, improves stability over similar compositions that do not contain radical scavenger, per comparative examples K and L. Comparative example J when compared to comparative example S, may demonstrate that a composition containing radical scavenger, per comparative example J, provides for better stability than a composition which does not contain radical scavenger even though that composition contains a comparatively higher level of chelating agent, per comparative example S.

Comparative example K does not contain any stabilizers (i.e. no radical scavenger and no chelating agent). It is comparable in all other ways to comparative example J. The stability of the viscosity of comparative example K is significantly reduced as compared to comparative example J.

Comparative example L demonstrates the necessity for the presence of both a chelating agent and radical scavenger. Exclusion of the radical scavenger in this formulation, even in the presence of chelating agent showed a marginal increase in viscosity stability in comparison to comparative example K.

With regard to comparative example S, it is expected that this formula will exhibit similar stability to comparative example L despite its higher level of chelating agent. It is believed that the chelating agent alone will not stabilize viscosity, as it does not act to stop degradation of the thickener by hydrogen peroxide. Moreover, the higher pH will likely exacerbate the thickener degradation as hydrogen peroxide itself becomes less stable (noting that hydrogen peroxide stability decreases drastically above a pH of 5).

Observations are made of exemplary compositions and are described as follows.

Evaluation of bubbling of exemplary compositions is conducted as follows. A 0.25% solution of catalase (from bovine liver from Sigma Aldrich at 2,000-5,000 units/mg protein) in DI water is prepared. The solution is sprayed onto dry, clean, vertical and horizontal stainless-steel surfaces (i.e., the "target surface").

An exemplary composition to be tested is sprayed from a distance of at least 8 inches from the target surface in one smooth pass from left to right. Formulas were sprayed on areas with and without catalase in order compare positive, negative, and false positive reactions. The exemplary composition is sprayed from a pump-up sprayer with a fan spray tip and pumped to a maximum pressure between 50-60 psi.

Observations of the positive reaction, air entrainment and bubble dissipation were made immediately following application. Observations include the following.

Exemplary composition A—Despite its high viscosity, this formula displays high shear thinning behavior that allows it to be sprayed in a wide fan configuration. The formula clings to vertical surfaces without running or dripping when applied in a uniform coating. Practically no bubbles are formed upon spraying the formula and those that do quickly rupture. The positive reaction of Example A with catalase is clearly visible.

Exemplary composition B—this composition exhibits bubbling similar to that of example A, which is described above. The compositions of example B is directly comparable to that of example A, with one exception—example B comprises less thickener. Thus, it is believed that a reduction in thickener does not have a demonstrable effect on bubbling.

Exemplary example C—When compared to Example A, Example C exhibits less shear thinning when sprayed onto the target surface. Example C clings to vertical surfaces without running or dripping when applied in a uniform coating. The positive reaction of Example C is visible, but less pronounced than that of Example A in areas where there is less catalase on the target surface.

Comparative example J—When attempting to spray at high pressure in a fan configuration, the formula initially emerges from the spray tip in a fan pattern but immediately falls back onto itself creating a stream rather than a broad fan-shaped pattern. In addition, the high-pressure spray entrains a large amount of air that creates a false positive reaction.

Comparative examples K through S—These formulations produce similar spray performance and positive reaction quality as comparative example J.

The ability of biofilm-detecting compositions to detect biofilm is assessed as follows.

18×18 mm glass carriers are added to beakers containing 20 ml of liquid growth media (Tryptic soy broth for bacteria, Saboraud dextrose broth for yeast).

24 to 48 hour cultures of test microorganisms identified in Table 3 are used to inoculate the liquid media containing the glass carriers.

TABLE 3

| Test Microorganism | CFU/Carrier |
|---|---|
| *Staphylococcus aureus* ATCC 6538 | 1.11E+06 |
| *Pseudomonas aeruginosa* ATCC | 1.36E+06 |
| *Candida albicans* ATCC 10231 | 3.12E+05 |
| *Listeria monocytogenes* ATCC 15313 | 1.34E+06 |
| *Salmonella enterica* ATCC 10708 | 1.02E+06 |
| *Lactobacillus acidophilus* ATCC 4356 | 1.60E+05 |

When the incubation period ends, biofilm laden glass carriers are gently rinsed with phosphate buffered saline to remove planktonic cells.

Rinsed carriers are placed in sterile petri dishes and treated with the composition to be tested. The test composition is delivered to the carrier located in the petri dishes using a pressurized spray bottle. Spray is applied from a distance of approximately 2 feet in a sweeping motion over the carrier.

Over a 5-minute period, treated slides are observed for effervescence.

A single carrier per each microorganism is enumerated to determine approximate initial microorganism load in colony forming units (CFU) per carrier (see Table 3, above).

*L. acidophilus* ATCC 4356, is grown under anaerobic conditions per microorganism growth requirements.

All bacteria carriers and enumeration plates are incubated at 36° C.±1° C.

All yeast carriers and enumeration plates are incubated at 30° C.±2° C.

When Example B is tested using this method, the following is observed. No reaction is observed over the entire observation period on control carriers that lack biofilm or that have an *L. acidophilus* (a catalase-negative biofilm). Any bubbles generated from spray shear dissipate instantly. All other organisms (all catalase-positive) react within seconds of applying Example B. Any bubbles generated from spray shear dissipate instantly.

Based upon the stability and observational studies, the following surprising observations of the exemplary compositions are made. First, it appears that viscosity stability in exemplary compositions that comprise solvent and coupling agent with the same levels of stabilizers are significantly improved over compositions comprising only surfactant for solubilizing radical scavenger. Second, it appears that the combination of surfactant, solvent and coupler provides a sprayable product that quickly dissipates any foaming not related to positive reaction. Third, it appears that low-foaming surfactant despite its innate nature provides enough foam volume and stability to easily identify a positive reaction with catalase.

Based upon the biofilm detection study, it is confirmed that exemplary composition A is capable of detecting a variety of different biofilms and does not react to a catalase-negative biofilm, thus acting as a good indicator of the presence of biofilm without generating a false positive bubbling reaction.

A first exemplary composition for use in detecting biofilm on a surface, the composition comprising:

(a) radical scavenger;
(b) solvent;
(c) thickener;
(d) hydrogen peroxide;
(e) chelating agent;
(f) coupling agent;
(g) low-foaming surfactant; and
(h) water.

A second exemplary composition according to the first exemplary composition, further comprising colorant.

A third exemplary composition according to either one of the first and second exemplary compositions, further comprising wetting agent.

A fourth exemplary composition according to any one of the foregoing exemplary compositions, further comprising wetting agent.

A fifth exemplary composition according to any one of the foregoing exemplary compositions, wherein the composition has a pH of from about 3 to about 7.

A sixth exemplary composition according to any one of the foregoing exemplary compositions, wherein the composition has a pH of from about 4.5 to about 5.5.

A seventh exemplary composition according to any one of the foregoing exemplary compositions, wherein the radical scavenger is selected from the group of: alkyl gallates, hindered phenols, hydroquinone, trihydroxy butyrophenone and combinations thereof.

An eighth exemplary composition according to any one of the foregoing exemplary compositions, wherein the radical scavenger is selected from the group of: butylated hydroxytoluene ("BHT"), butylated hydroxyanisole ("BHA"), tertiary butylhydroquinone ("TBHQ"), tocopherols, tocopherol ester derivatives and combinations thereof. Useful tocopherol ester derivatives may be selected from the group of: tocopheryl acetate, tocopheryl linoleate, tocopheryl nicotinate, tocopheryl succinate and combinations thereof.

A ninth exemplary composition according to any one of the foregoing exemplary compositions, wherein the radical scavenger is present in an amount of from about 0.001% to about 0.3% by weight of the composition.

A tenth exemplary composition according to any one of the foregoing exemplary compositions, wherein the solvent is selected from the group of: glycol ethers, glycol ether acetates, glycol diethers (glymes) and combinations thereof.

An eleventh exemplary composition according to any one of the foregoing exemplary compositions, wherein the solvent is selected from the group of: ethylene glycol propyl ether, ethylene glycol n-butyl ether, diethylene glycol methyl ether, diethylene glycol n-butyl ether, diethylene glycol ethyl ether, triethylene glycol methyl ether, triethylene glycol ethyl ether, triethylene glycol n-butyl ether, propylene glycol methyl ether, propylene glycol n-propyl ether, dipropylene glycol methyl ether, dipropylene glycol n-propyl ether, tripropylene glycol methyl ether, and polyethylene glycol phenyl ether; glycol ether acetates, such as propylene glycol methyl ether acetate and dipropylene glycol methyl ether acetate; and glycol diethers (glymes), such as ethylene glycol dimethyl ether, ethylene glycol diethyl ether, diethylene glycol dimethyl ether, diethylene glycol diethyl ether, triethylene glycol dimethyl ether, tetraethylene glycol dimethyl ether, dipropylene glycol dimethyl ether, poly(ethylene glycol) dimethyl ether and combinations thereof.

A twelfth exemplary composition according to any one of the foregoing compositions, wherein the solvent is present in an amount of from about 5% to about 22% by weight of the composition.

A thirteenth exemplary composition according to any one of the foregoing exemplary compositions, wherein the thickener is selected from the group of: natural gums (such as xanthan gum, guar gum, and gellan gum), alginates (such as sodium alginate, potassium alginate, propylene glycol alginate, and ammonium alginate), cellulosic thickeners (such as carboxymethylcellulose and its sodium salt, hydroxyethyl cellulose, and hydroxypropyl methylcellulose), organic polymeric acid colloids (such as polyuronic acids, carboxypolymethylene compounds, polyester resins containing free carboxyl groups (such as partially hydrolyzed polyacrylates or polymethacrylates, polyacrylic acid, polymethacrylic acid, copolymers of unsaturated esters and acids (such as copolymers of methylmethacrylate and methacrylic acid and copolymers of acrylic acid crosslinked with polyallyl sucrose))), clays (such as montmorillonite, kaolin, illite, saponite, bentonite, hectorite, beidellite, stevensite, attapulgite, sepiolite, laponite), hydrophobically modified fumed silicas and combinations thereof.

A fourteenth exemplary composition according to any one of the foregoing compositions, wherein the thickener is present in an amount of from about 0.1% to about 1% by weight of the composition.

A fifteenth exemplary composition according to any one of the foregoing compositions, wherein the chelating agent is selected from the group of: phosphonic acid, phosphonic acid salts, polyamino phosphonic acid, polyamino phosphonic acid and salts thereof.

A sixteenth exemplary composition according to any one of the foregoing compositions, wherein the chelating agent is selected from the group of: phosphonic and polyamino phosphonic acids (such as 1-hydroxyethilidene 1,1-diphosphonic acid, aminotris (methylene phosphonic acid), diethylenetriamine penta(methylene phosphonic acid), bis(hexamethylene triamine penta(methylenephosphonic acid)), ethylidenediamine tris(methylene phosphonic acid), hexamethylenediamine tetra(methylene phosphonic acid), and their potassium and sodium salts), water soluble alkali metal stannates (such as sodium stannate) and combinations thereof.

A seventeenth exemplary composition according to any one of the foregoing compositions, wherein the chelating agent is present in an amount of from about 0.01% to about 0.1% by weight of the composition.

An eighteenth exemplary composition according to any one of the foregoing compositions, wherein the coupling agent is selected from the group of: sodium, potassium and ammonium salts of alkyl aryl sulfonates (such as xylene sulfonate, toluene sulfonate and cumene sulfonate) and combinations thereof.

A nineteenth exemplary composition according to any one of the foregoing compositions, wherein the coupling agent is present in an amount of from about 1% to about 10% by weight of the composition.

A twentieth exemplary composition according to any one of the foregoing compositions, wherein the low-foaming surfactant is selected from the group of: low-foaming linear amine oxide, low-foaming branched amine oxide, alcohol alkoxylates (e.g., end-capped alcohol alkoxylates), alkyl polyglycosides, alkanoate salts and combinations thereof.

A twenty-first exemplary composition according to any one of the foregoing compositions, wherein the low-foaming surfactant is selected from the group of: low-foaming linear amine oxide, low-foaming branded amine oxide and combinations thereof.

A first exemplary method for detecting biofilm on a surface, wherein the method is characterized by low to no false positives, the method comprising:
  (i) spraying onto the surface a composition according to any one of the first through twenty-first exemplary compositions;
  (ii) allowing the composition to act for a period of time; and
  (iii) visually inspecting the surface for bubbles/foam.

A second exemplary method according to the first exemplary method, comprising spraying the exemplary composition onto the surface from a minimum distance of about 8 inches.

A third exemplary method according to either one of the first or second exemplary methods, comprising spraying onto the surface the exemplary composition using a side-to-side motion.

A fourth exemplary method according to any of the foregoing exemplary methods, comprising visually inspecting the surface within two minutes of application of the exemplary composition.

A fifth exemplary method according to any of the foregoing exemplary methods, comprising rinsing the surface with water after step (iii).

A sixth exemplary method according to any of the foregoing exemplary methods, wherein the surface is made from substances selected from the group of: metallic surfaces, such as aluminum, steel, or stainless steel; or surfaces such as glass, ceramic or porcelain, plastic surfaces, such as thermoplastic or thermosetting polymers, for example, epoxy resin and combinations thereof.

A seventh exemplary method according to any of the foregoing exemplary methods, wherein the surface is made from substances selected from the group of: Al 1100, Al 5052, Al 3003, stainless steel, carbon steel, SS 304, SS 316, HDPE, LDPE, polypropylene, PVC, PTFE, Acetyl, polycarbonate, mylar, Viton, BUNA-N and combinations thereof.

An eighth exemplary method according to any of the foregoing exemplary methods, wherein the surface is selected from the group of: horizontal surface, vertical surface, cracks, crevasses and combinations thereof.

A first exemplary device for detecting biofilm on a surface, the device comprising a nozzle and containing biofilm-detecting composition according to any one of the first through twenty-first exemplary compositions, wherein the device is configured to dispense the composition through the nozzle.

A second exemplary device for detecting biofilm on a surface, wherein the nozzle is configured to dispense the composition via a fan of droplets using a spray angle of from about 70 degrees to about 110 degrees.

A third exemplary device for detecting biofilm on a surface according to either one of the first or second exemplary devices, wherein the device is configured to deliver the composition to the surface via a flow rate from about 0.1 to about 0.20 gallons per minute.

A fourth exemplary device for detecting biofilm on a surface according any one of the foregoing exemplary devices, wherein the device is configured to dispense the composition using a using spray pressure of from about 40 to about 50 pounds per square inch ("PSI").

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

We claim:

1. An aqueous biofilm-detecting composition, wherein the composition is reactive to biofilm on a hard surface, the biofilm-detecting composition comprising:
   (a) radical scavenger, wherein the radical scavenger is selected from the group consisting of: alkyl gallates, hindered phenols, hydroquinone, trihydroxy butyrophenone and combinations thereof;
   (b) solvent, wherein the solvent is selected from the group consisting of: glycol ethers, glycol ether acetates, glycol diethers (glymes) and combinations thereof;
   (c) thickener;
   (d) hydrogen peroxide;
   (e) chelating agent, wherein the chelating agent is selected from the group consisting of: phosphonic acids, phosphonic acid salts, polyamino phosphonic acids, polyamino phosphonic acid salts, water soluble alkali metal stannates and combinations thereof;
   (f) coupling agent, wherein the coupling agent is selected from the group consisting of sodium, potassium and ammonium salts of alkyl aryl sulfonates and combinations thereof; and
   (g) Low-Foaming surfactant, wherein the Low-Foaming surfactant has a structure according to Formula I:

wherein:
   R1 is selected from an alkyl group having between from 6 and to 22 carbon atoms, or a substituted aryl group having between from 7 and to 22 carbon atoms,
   R2 is comprises from 0 to 7 moles of alkoxylated units, and
   R3 and R4 are each at least one alkoxylated unit; and further wherein and the total number of alkoxylated units present in R3 and R4 is from about 2 to about 30.

2. The biofilm-detecting composition of claim 1, comprising by weight percentage of the composition:
   (a) from about 0.001% to about 0.3% radical scavenger;
   (b) from about 5% to about 22% solvent;
   (c) from about 0.01% to about 1% thickener;
   (d) from about 1% to about 10% hydrogen peroxide;
   (e) from about 0.01% to about 0.1% chelating agent;
   (f) from about 1% to about 10% coupling agent; and
   (g) from about 0.1% to about 3% Low-Foaming surfactant.

3. The biofilm-detecting composition of claim 2, comprising by weight percentage of the composition:
   (a) from about 0.08% to about 0.1% radical scavenger; and
   (e) from about 0.05% to about 0.07% chelating agent.

4. The biofilm-detecting composition of claim 1, wherein the Low-Foaming surfactant has a structure according to Formula II:

wherein:
   R1 is selected from an alkyl group having between 6 and 22 carbon atoms or a substituted aryl group having between 7 and 22 carbon atoms or,
   R3 and R4 are each at least one alkoxylated unit, and further wherein the total number of alkoxylated units present in R3 and R4 is about 2 to 30.

5. The biofilm-detecting composition of claim 1, wherein the surfactant has a hydrophobic-lipophilic balance of from about 6 to less than 10.

6. The biofilm-detecting composition of claim 1, further comprising wetting agent.

7. The biofilm-detecting composition of claim 1, wherein the composition has a pH of from about 3 to less than 6.

8. The biofilm-detecting composition of claim 1, wherein the radical scavenger is selected from the group consisting of: butylated hydroxytoluene, butylated hydroxyanisole, tertiary butylhydroquinone, tocopherols, tocopherol ester derivatives and combinations thereof.

9. The biofilm-detecting composition of claim 1, wherein the biofilm-detecting composition is substantially free of High-Foaming surfactant that has:
(a) a hydrophobic-lipophilic balance (HLB) of greater than 10; and/or
(b) a Ross-Miles Initial Foam Height of greater than 5 cm.

10. A method of detecting biofilm on a hard surface, comprising:
(a) spraying onto the surface a composition according to claim 1;
(b) allowing the composition to act for a period of time; and
(c) visually inspecting the surface for bubbles/foam.

11. An aqueous biofilm-detecting composition, wherein the composition is reactive to biofilm on a surface, the biofilm-detecting composition comprising by weight percentage of the composition:
(a) from about 0.001% to about 0.3% radical scavenger selected from the group consisting of: butylated hydroxytoluene ("BHT"), butylated hydroxyanisole ("BHA"), tertiary butylhydroquinone ("TBHQ"), tocopherols, tocopherol ester derivatives and combinations thereof;
(b) from about 5% to about 22% solvent, wherein the solvent is selected from the group consisting of: glycol ethers, glycol ether acetates, glycol diethers (glymes) and combinations thereof;
(c) from about 0.01% to about 1% thickener;
(d) from about 1% to about 10% hydrogen peroxide;
(e) from about 0.01% to about 0.1% chelating agent selected from the group consisting of: phosphonic acids, polyamino phosphonic acids, phosphonic acid salts, polyamino phosphonic acid salts, water soluble alkali metal stannates and combinations thereof;
(f) from about 1% to about 10% coupling agent selected from the group consisting of sodium, potassium and ammonium salts of alkyl aryl sulfonates and combinations thereof; and
(g) from about 0.1% to about 3% Low-Foaming surfactant that has:
1) a hydrophobic-lipophilic balance (HLB) of from about 6 to about 13; and/or
2) a Ross-Miles Initial Foam Height of from about 0.2 cm to about 4 cm;
with the proviso that a Low-Foaming surfactant that has an HLB of greater than 10 must have a Ross-Miles Initial Foam Height of from about 0.2 cm to about 4 cm.

12. A method of detecting biofilm on a hard surface, comprising:
(a) spraying onto the surface a composition according to claim 11;
(b) allowing the composition to act for a period of time; and
(c) visually inspecting the surface for bubbles/foam.

* * * * *